(12) United States Patent
Appenzeller et al.

(10) Patent No.: US 9,149,316 B2
(45) Date of Patent: Oct. 6, 2015

(54) ANCHOR-IN-ANCHOR SYSTEM

(71) Applicant: DePuy Synthes Products, Inc., Raynham, MA (US)

(72) Inventors: Andreas Appenzeller, Oberdorf (CH); Daniel Fluri, Oberdorf (CH); Peter Steiger, Herzogenbuechse (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/972,010

(22) Filed: Aug. 21, 2013

(65) Prior Publication Data

US 2014/0058457 A1    Feb. 27, 2014

Related U.S. Application Data

(60) Provisional application No. 61/691,961, filed on Aug. 22, 2012.

(51) Int. Cl.
*A61B 17/04*  (2006.01)
*A61B 17/86*  (2006.01)
*A61F 2/08*  (2006.01)
*A61B 17/68*  (2006.01)
*A61B 17/72*  (2006.01)
*A61B 17/80*  (2006.01)

(52) U.S. Cl.
CPC ............... *A61B 17/864* (2013.01); *A61B 17/68* (2013.01); *A61B 17/8605* (2013.01); *A61B 17/8685* (2013.01); *A61B 17/686* (2013.01); *A61B 17/7233* (2013.01); *A61B 17/8047* (2013.01); *A61B 17/8695* (2013.01)

(58) Field of Classification Search
USPC .................................................. 606/305–308
See application file for complete search history.

(56) References Cited

U.S. PATENT DOCUMENTS

| | | | |
|---|---|---|---|
| 5,797,918 A | 8/1998 | McGuire et al. |
| 6,270,499 B1 | 8/2001 | Leu |
| 6,629,998 B1 | 10/2003 | Lin |
| 7,637,928 B2 | 12/2009 | Fernandez |
| 8,343,196 B2 | 1/2013 | Schneider |
| 8,574,268 B2 | 11/2013 | Chan et al. |
| 8,758,346 B2 | 6/2014 | Koay et al. |

(Continued)

FOREIGN PATENT DOCUMENTS

| | | |
|---|---|---|
| CN | 1620271 A | 5/2005 |
| CN | 101677863 A | 3/2010 |

(Continued)

OTHER PUBLICATIONS

International Patent Application No. PCT/US2013/055939: International Search Report and Written Opinion dated Oct. 31, 2013, 9 pages.

(Continued)

*Primary Examiner* — Sameh Boles
(74) *Attorney, Agent, or Firm* — Baker & Hostetler LLP

(57) ABSTRACT

An anchor-in-anchor fixation system is provided for securing underlying structure, such as bone. The fixation system includes a linkage that defines first and second bores, a first bone anchor having a shaft for fixation to underlying bone, and a head that is configured to attach to the linkage in the first bore, and a second bone anchor having a shaft for fixation to underlying bone and a head that is configured to attach to the linkage in the second bore.

20 Claims, 15 Drawing Sheets

(56) References Cited

U.S. PATENT DOCUMENTS

| | | |
|---|---|---|
| 8,845,698 B2 | 9/2014 | Schneider |
| 8,852,245 B2 | 10/2014 | Schneider |
| 8,876,873 B2 | 11/2014 | Schneider |
| 2002/0128712 A1 | 9/2002 | Michelson |
| 2005/0107791 A1 | 5/2005 | Manderson |
| 2006/0189991 A1 | 8/2006 | Bickley |
| 2010/0057132 A1 | 3/2010 | Graham et al. |
| 2010/0076496 A1 | 3/2010 | Fernandez |
| 2010/0274296 A1 | 10/2010 | Appenzeller et al. |
| 2010/0312280 A1 | 12/2010 | Overes et al. |
| 2010/0312286 A1 | 12/2010 | Dell'Oca |
| 2011/0022066 A1 | 1/2011 | Sevrain |
| 2012/0143262 A1 | 6/2012 | Jensen et al. |
| 2014/0180345 A1 | 6/2014 | Chan et al. |
| 2015/0018889 A1 | 1/2015 | Schneider |

FOREIGN PATENT DOCUMENTS

| | | |
|---|---|---|
| FR | 2718014 | 10/1995 |
| JP | 54-118566 | 8/1979 |
| JP | 2001/252283 | 9/2001 |
| JP | 2008/510517 | 4/2008 |
| WO | WO 2004/008980 | 1/2004 |
| WO | WO 2004/078049 | 9/2004 |
| WO | WO 2007/098288 A2 | 8/2007 |
| WO | WO 2009/120852 A2 | 10/2009 |
| WO | WO 2010/017357 | 2/2010 |
| WO | WO 2011/085272 | 7/2011 |
| WO | WO 2011/155931 | 12/2011 |
| WO | WO 2012/102726 | 8/2012 |

OTHER PUBLICATIONS

U.S. Appl. No. 60/955,506, filed Aug. 13, 2007, Chan et al.
U.S. Appl. No. 61/000,907, filed Oct. 30, 2007, Koay et al.
U.S. Appl. No. 61/084,281, filed Jul. 29, 2008, Fernandez et al.
U.S. Appl. No. 61/242,102, filed Sep. 14, 2009, Koay et al.

ANCHOR-IN-ANCHOR SYSTEM

CROSS-REFERENCE TO RELATED APPLICATIONS

This claims the benefit of U.S. patent application Ser. No. 61/691,961 filed Aug. 22, 2012, the disclosure of which is hereby incorporated by reference as if set forth in its entirety herein.

TECHNICAL FIELD

The present disclosure relates generally to orthopedics, an in particular relates to fixation systems and associated surgical methods and procedures for using same.

BACKGROUND

A variety of fixation devices for the reduction of bone or bone fragments are well known. For instance, external bone fixation devices, or external fixators, are used to reduce fractures of the long bones in the human body. Internal bone fixation devices, such as bone plates, are also commonly used to reduce bone fractures. Spinal fixation devices including intervertebral implants, spinal rods, and the like, are used to replace intervertebral discs, fuse or align adjacent vertebrae, and address other spinal issues.

A large number of fixation devices are attached to underlying bone using bone anchors, which can include screws, pins, nails, and the like. For instance, a typical bone plate includes screw holes that accommodate bone screws which are drilled into underlying bone on opposing sides of a fracture to join bone segments together. A typical cervical spine implant can likewise include screw holes that accommodate screws which are drilled into adjacent vertebral bodies in order to fix the position of the implant. Unfortunately, the attachment of fixation devices to the underlying bone can become compromised if, for instance, the screw becomes dislodged from the bone during normal anatomical function.

Referring to FIGS. 1A-B, a conventional anchor-in-anchor fixation system 20 includes a first bone anchor 22 that includes a first head 28 and a first shaft 26 that extends from the first head 28 and is integral and monolithic with the first head 28, and a second bone anchor 24 that includes a second head 44 and a second shaft 42 that extends from the second head 44 and is integral and monolithic with the second head 44. The first bone anchor 22 defines a bore 40 that extends through the first head 28 along a direction oblique to the first shaft 26. The bore 40 is sized greater than the second shaft 42, such that the second shaft 42 passes through the bore 40. The bore 40 can be threaded, and sized substantially equal to the second head 44, which can also be threaded, such that the second head 44 threadedly mates with the first head 28 in the bore 40. Thus, the second shaft 42 extends along a direction oblique with respect to the first shaft 26, which creates a stable triangular load bearing plane that allows the anchor-in-anchor fixation system 20 to withstand higher forces and prevent subsidence or migration with respect to single anchors.

As illustrated in FIG. 1D, the anchor-in-anchor fixation system 20 can join a pair of bone fragments 45a and 45b of a fractured bone 45 together, for instance when repairing the fractured bone 45, and can further fix an implant to the bone 45. The bone 45 can be a long bone, the first bone fragment 45a can be a diaphysis, or shaft, of the long bone, and the second bone fragment 45b can be a metaphysis of the long bone, though it is appreciated that the bone 45 can be any suitable bone as desired. As illustrated in FIG. 1C, the anchor-in-anchor fixation system 20 can be used to attach an implant to the bone 45. In particular, one of the bone anchors, such as the first bone anchor 22, can be driven through a bone plate 47 and into the bone 45, and the second bone anchor 24 can be driven through the bore 40 of the first head 28 and into the bone 45. As illustrated in FIG. 1D, the anchor-in-anchor fixation system 20 can be used to attach an implant in the medullary canal of the bone 45. In particular, one of the bone anchors, such as the first bone anchor 22, can be driven into the bone 45 and through an aperture of an intramedullary nail 49, and the second bone anchor 24 can be driven through the bore 40 of the first head 28 and into the bone 45.

SUMMARY

In accordance with one embodiment, a linkage is configured for use in an anchor-in-anchor system. The linkage includes a linkage body defining an open upper end, a lower end, and at least one side, the at least one side defining an internal void that extends between the upper and lower ends, the upper and lower ends spaced along a central axis of the linkage body. The lower end of the linkage body defines a first bore that is open to the internal void, the first bore extending along a central axis, the lower end threaded so as to purchase with complementary threads of a first head of a first bone anchor so as to attach the first bone anchor to the linkage. The linkage body includes an interior surface that defines a second bore that extends through the linkage body along a central axis that is oblique to the central axis of the first bore. The interior surface is threaded so as to purchase with complementary threads of a second head of a second bone anchor so as to attach the second bone anchor to the linkage.

BRIEF DESCRIPTION OF THE DRAWINGS

The foregoing summary, as well as the following detailed description of the preferred embodiments of the application, will be better understood when read in conjunction with the appended drawings. For the purposes of illustrating the anchor-in-anchor system, there are shown in the drawings preferred embodiments. It should be understood, however, that the application is not limited to the precise arrangements and instrumentalities illustrated in the drawings, in which.

DETAILED DESCRIPTION

Figure 1A:
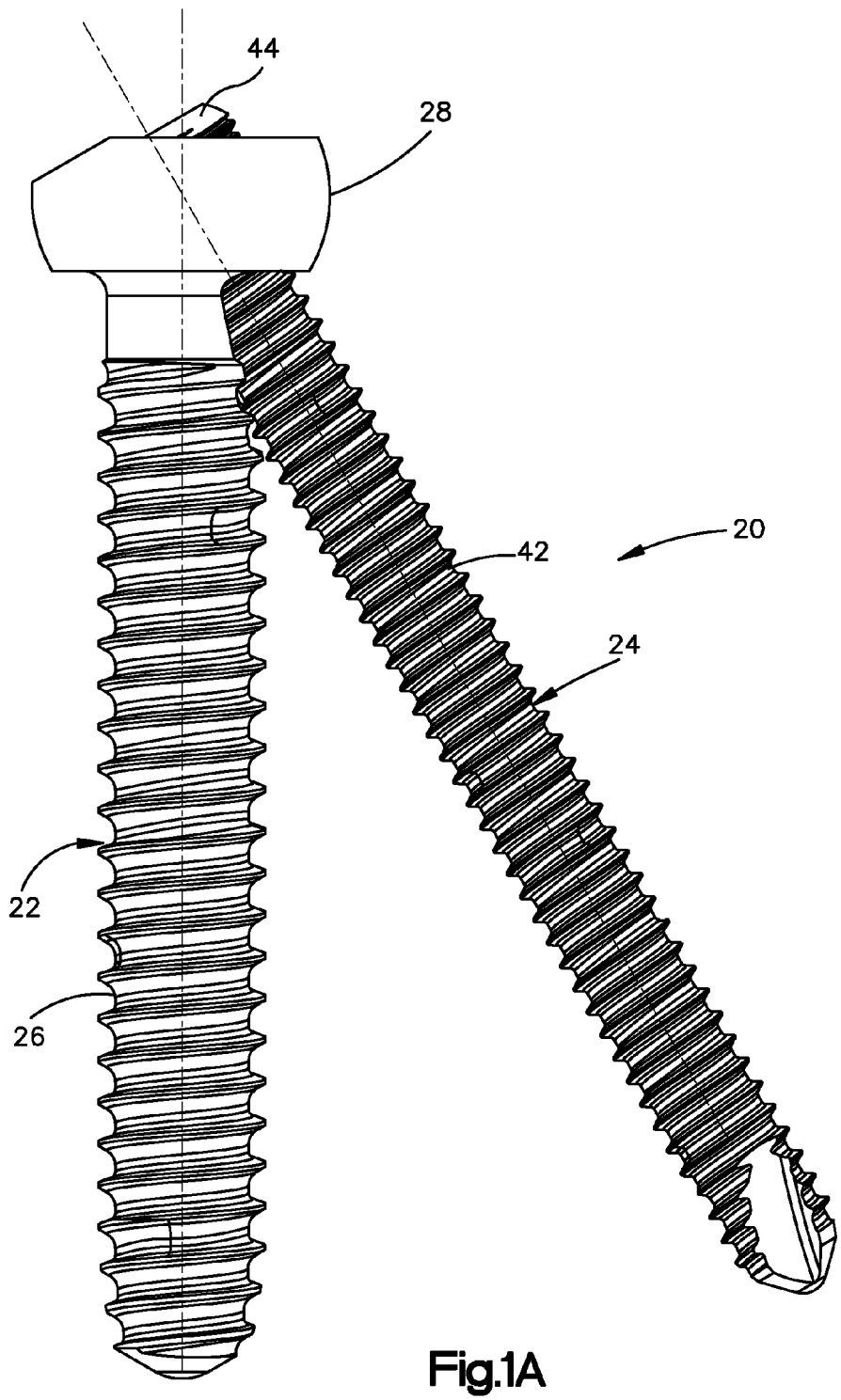
FIG. 1A is a side elevation view of an anchor-in-anchor system constructed in accordance with the prior art.

Certain terminology is used in the following description for convenience only and is not limiting. The words "right," "left," "top," and "bottom" designate in the drawings to which reference is made. The words "inwardly" and "outwardly" refer to directions toward and away from, respectively, the geometric center of the device and designated parts thereof. The words "anterior," "posterior," "superior," "inferior," and related words and/or phrases designate preferred positions and orientations in the human body to which reference is made and are not meant to be limiting. The terminology includes the above-listed words, derivatives thereof and words of similar import.

Figure 2:
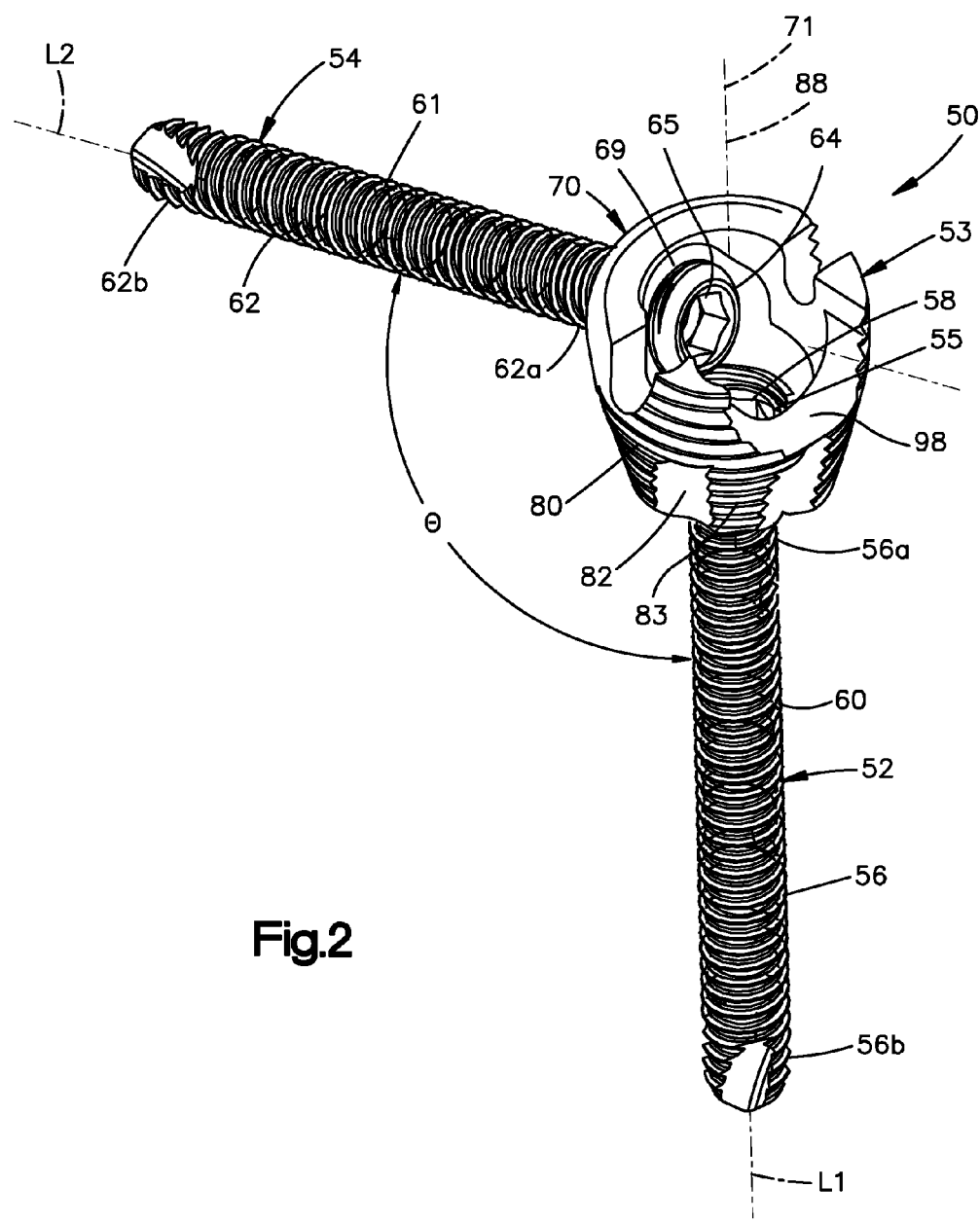
FIG. 2 is a perspective view of an anchor-in-anchor system constructed in accordance with one embodiment, including a first anchor, a second anchor, and a linkage that is attachable to the first and second anchors.

Referring to FIG. 2, an anchor-in-anchor fixation system 50 is illustrated as attached to an underlying structure or bone. The fixation system 50 is illustrated as a bone fixation system in accordance with one example embodiment that includes a first or primary bone fixation element or bone anchor 52, a second or auxiliary bone fixation element or bone anchor 54 that is configured to be coupled with respect to the first bone anchor 52, and a linkage 53 that is configured to attach to both the first and second bone anchors 52 and 54, thereby coupling the first and second bone anchors 52 and 54 with respect to each other. The bone fixation system 20 can be used to securely fasten auxiliary fixation devices such as external fixators, internal bone fixation devices, spinal fixation devices, and the like, to underlying bone. Unless otherwise indicated, the bone fixation system 20 and its components can be manufactured from any suitable biocompatible material known in the art including but not limited to titanium, titanium alloy such as TAN, stainless steel, reinforced plastics, allograft bone, and the like, unless otherwise indicated.

The first bone anchor 52 includes a first shaft 56 that extends longitudinally along, and is elongate along, a first central axis L1. The first shaft 56 defines a proximal or upper end 56a and a distal or lower end 56b that is spaced from the upper end 56a along the first central axis L1. The first bone anchor 52 can further include a first head 58 that is coupled to the upper end 56a. The first head 58 can be integral and monolithic with the first shaft 56, and can define external threads 59 (see FIG. 4A) so as to be threadedly and removably attachable to the linkage 53. The threads 59 of the first head 58 can be substantially cylindrical, or can be tapered inwardly, for instance either straight or curved, toward the first central axis L1 as the first head 58 extends along a distal direction from the first head 58 toward the first shaft 56.

Figure 1B:
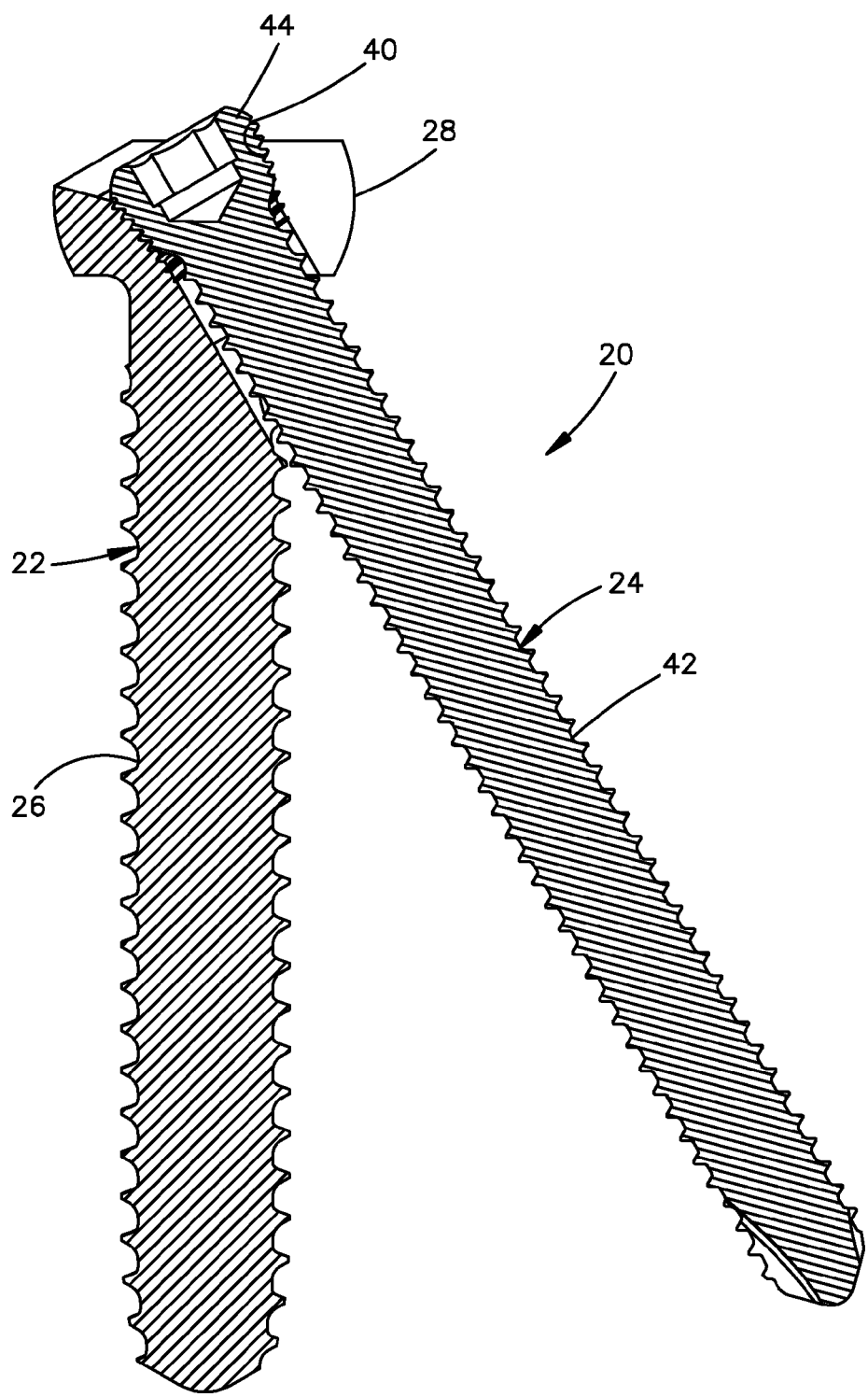
FIG. 1B is a sectional side elevation view of the anchor-in-anchor system illustrated in FIG. 1A.
Figure 1C:
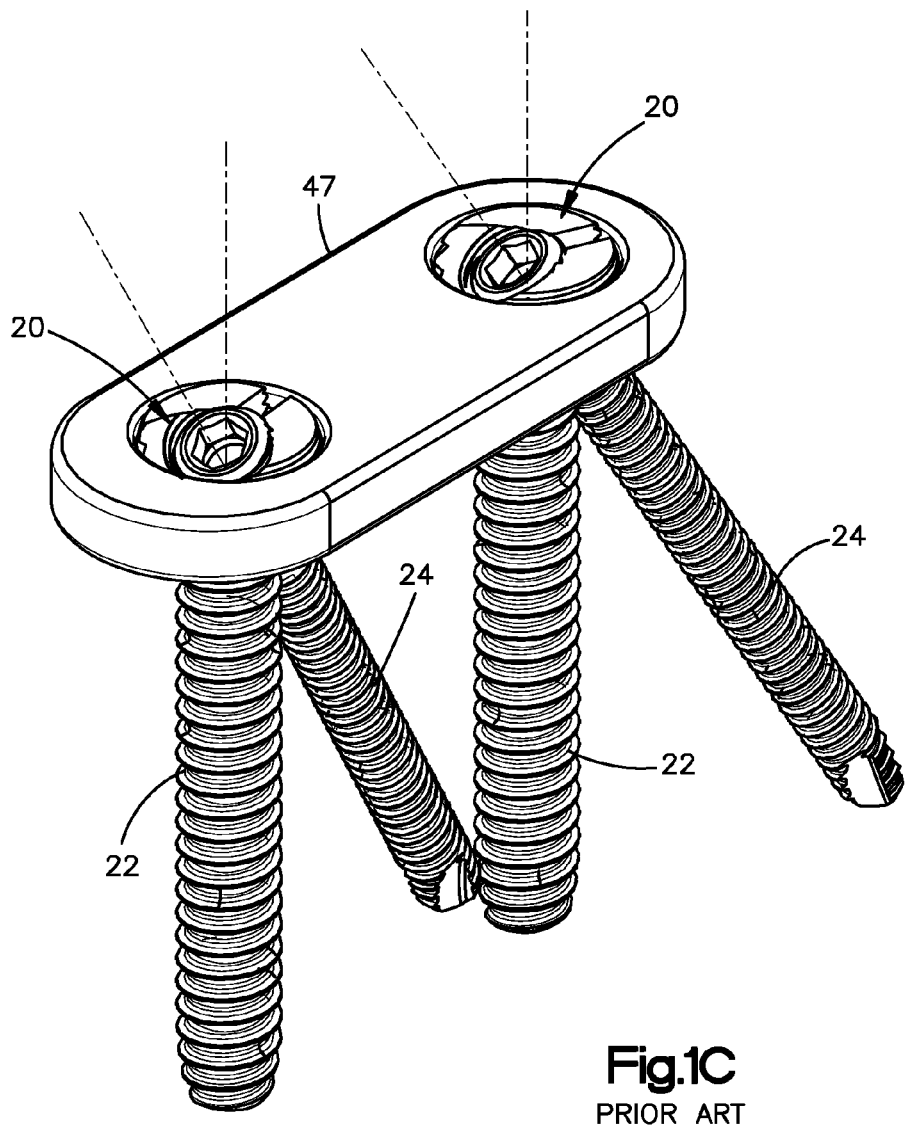
FIG. 1C is a side elevation view of the anchor-in-anchor system illustrated in FIG. 1A, attached to a bone plate.
Figure 1D:
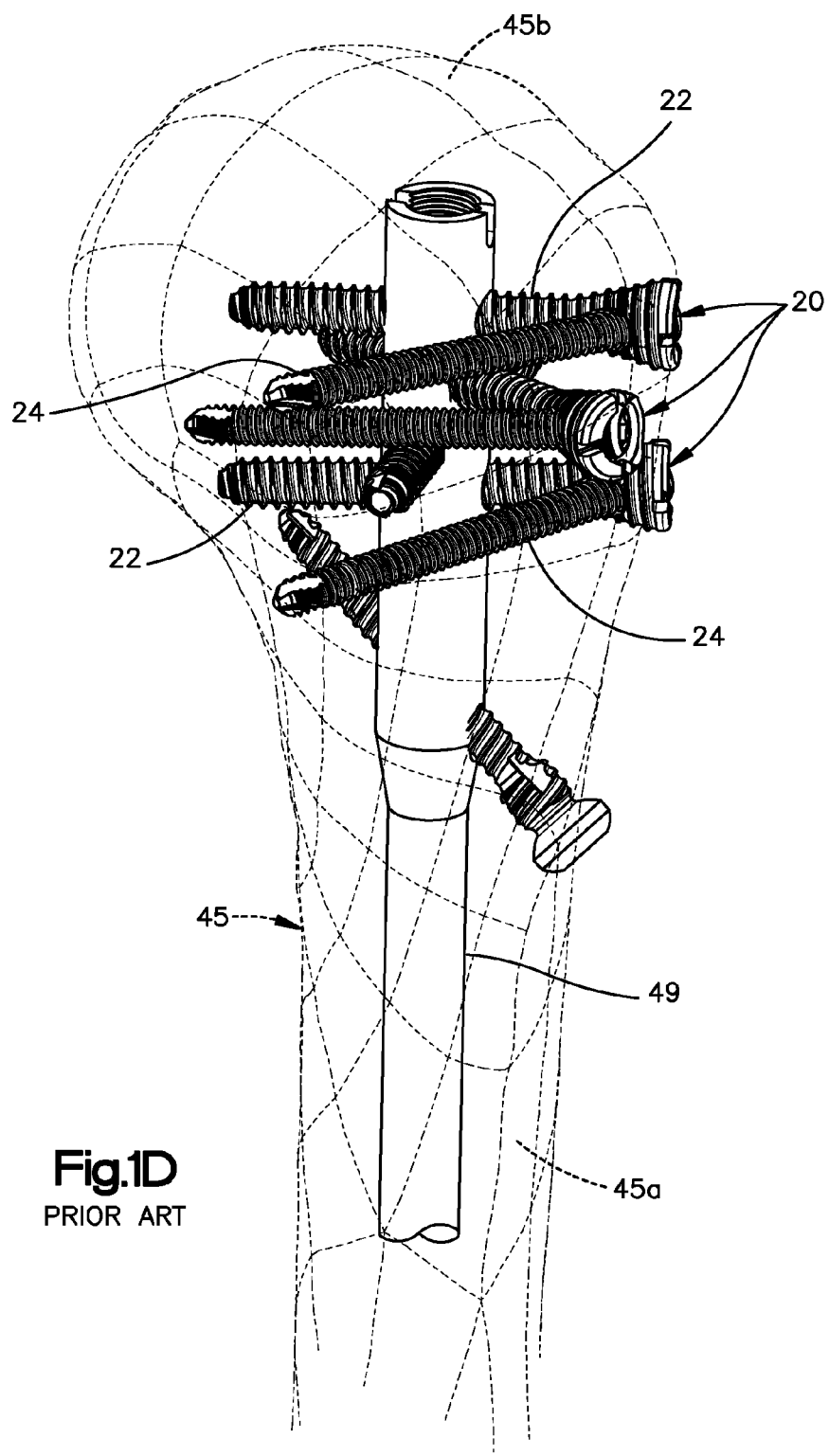
FIG. 1D is a side elevation view of the anchor-in-anchor system illustrated in FIG. 1A, attached to an intramedullary nail.

The first shaft 56 can define a plurality of external threads 60 that are disposed between the upper end 56a and the lower end 56b, and can extend from the upper end 56a to the lower end 56b, and are configured to threadedly engage an underlying bone as described above with reference to FIG. 1D. Thus, any portion of the first shaft 56 can be threaded as desired. For instance, a majority or substantial entirety of the first shaft 56 can be threaded. Alternatively, as will be described in more detail below, the first shaft 56 can be threaded at one or more discrete locations. It should thus be appreciated that the first bone anchor 52 can provide as a locking screw as illustrated, though it should be appreciated that the first bone anchor can alternatively be provided as a compression screw, a nail, rivet, or pin whose shaft is smooth or ribbed, as desired.

The first bone anchor 52 can further include a first drive member 55 that is carried by the first head 58 and is configured to mate with a driving instrument, such as a screw driver, that applies a torsional force to the first bone anchor 52 and drives the first bone anchor 52 into the bone. In accordance with the illustrated embodiment, the first drive member 55 can be configured as a socket of any suitable size and shape that extends into the first head 58 along a direction substantially parallel to the first central axis L1. The socket is configured to receive a driving end of the driving instrument. Alternatively, the first drive member 55 can be configured as a protrusion that is received by the driving instrument.

The second bone anchor 54 includes a second shaft 62 that extends longitudinally along, and is elongate along, a second central axis L2. The second shaft 62 that defines a proximal or upper end 62a and a distal or lower end 62b that is spaced from the upper end 62a along the second central axis L2. The second bone anchor 54 can further include a second head 64 that is coupled to the upper end 62a. The second head 64 can be integral and monolithic with the second shaft 62, and can define external threads 69 so as to be threadedly and removably attachable to the linkage 53. When first and second the second bone anchors 52 and 54 are attached to the linkage 53, the second central axis L2 is angularly offset with respect to the first central axis L1 so as to define an angle θ between the first central axis L1 and the second central axis L2. As will be described in more detail below, at least one of the first and second bone anchors 52 and 54 is attachable to the linkage 53 at different angular orientations such that the angle θ is adjustable.

The second shaft 62 can define external threads 61 that are disposed between the upper end 62a and the lower end 62b, and can extend from the upper end 62a to the lower end 62b, and are configured to engage the underlying bone in the manner described above with respect to FIG. 1D. Thus, any portion of the second shaft 62 can be threaded as desired. For instance, a majority or substantial entirety of the second shaft 62 can be threaded. Alternatively, as will be described in more detail below, the second shaft 62 can be threaded at one or more discrete locations. It should thus be appreciated that the second bone anchor 54 can provide as a locking screw as illustrated, though it should be appreciated that the first bone anchor can alternatively be provided as a compression screw, a nail, rivet, or pin whose shaft is smooth or ribbed, as desired.

The second bone anchor 54 can further include a second drive member 65 that is carried by the second head 64 and is configured to mate with a driving instrument, such as a screw driver, that applies a torsional force to the second bone anchor 54 and drives the second bone anchor 54 into the bone. In accordance with the illustrated embodiment, the second drive member 65 can be configured as a socket of any suitable size and shape that extends into the second head 64 along a direction substantially parallel to the second central axis L2. The socket is configured to receive a driving end of the driving instrument. Alternatively, the second drive member 65 can be configured as a protrusion that is received by the driving instrument.

Figure 3A:
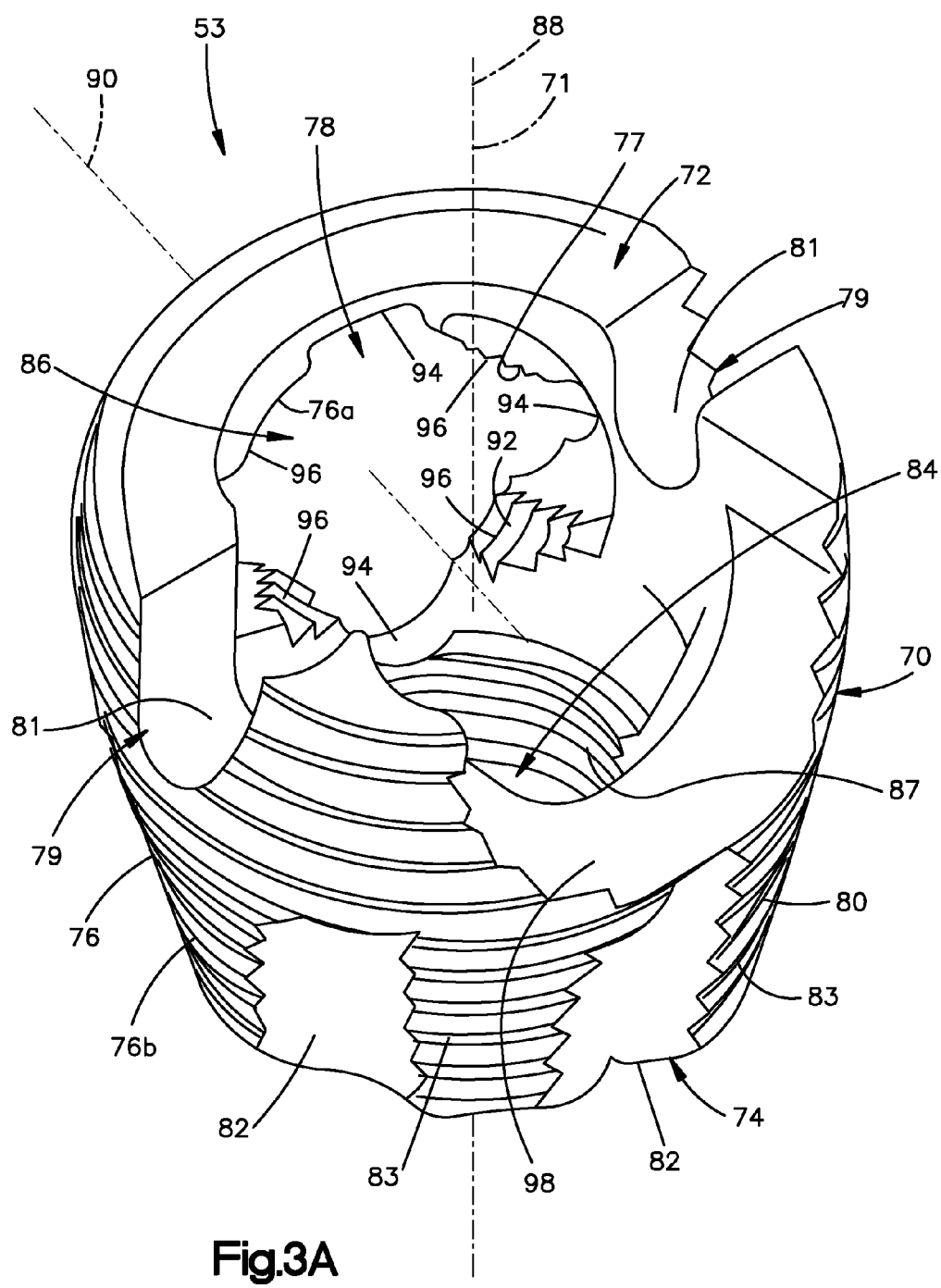
FIG. 3A is a top perspective view of the linkage illustrated in FIG. 2A.
Figure 3B:
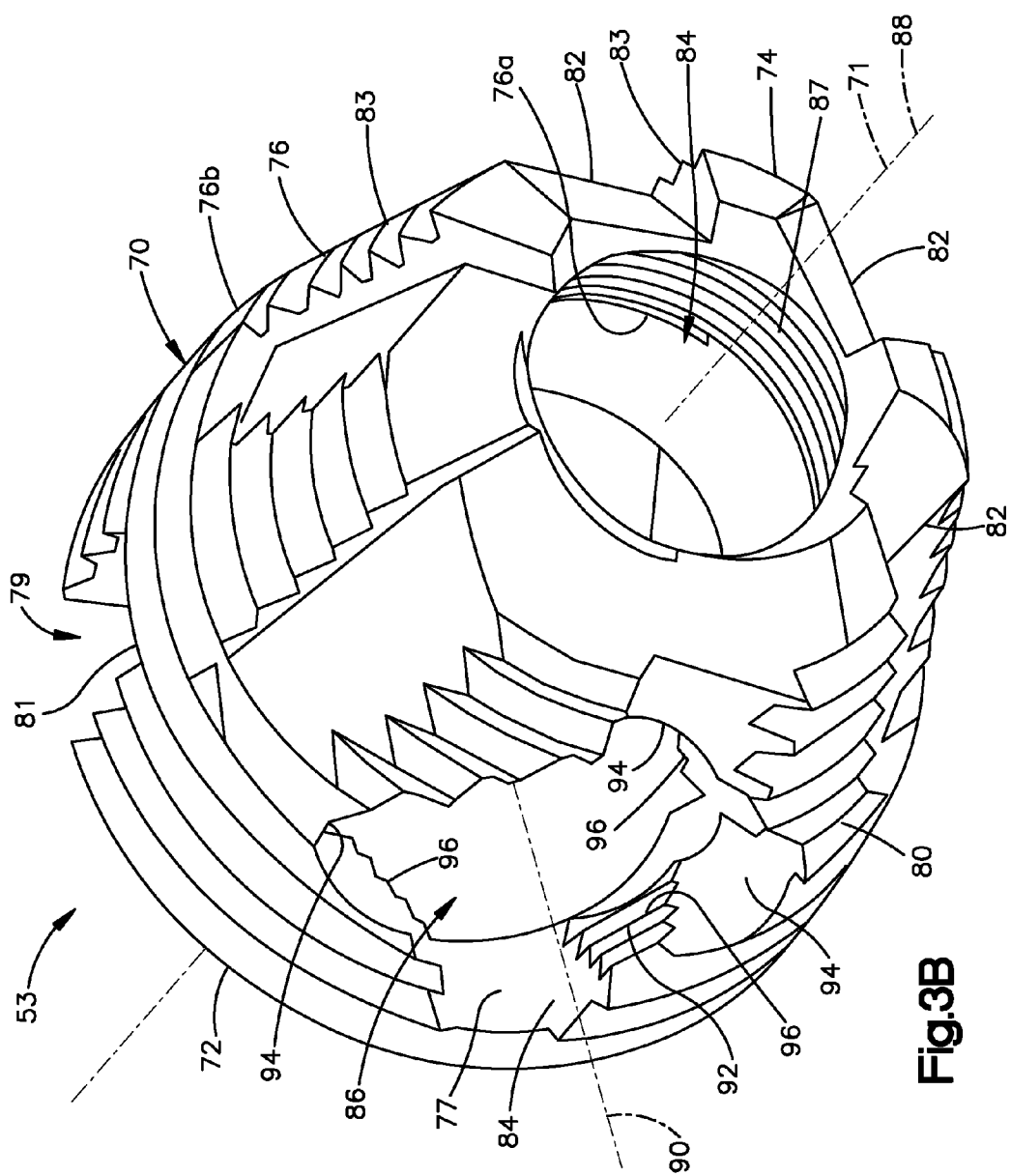
FIG. 3B is a bottom perspective view of the linkage illustrated in FIG. 3A.
Figure 3C:
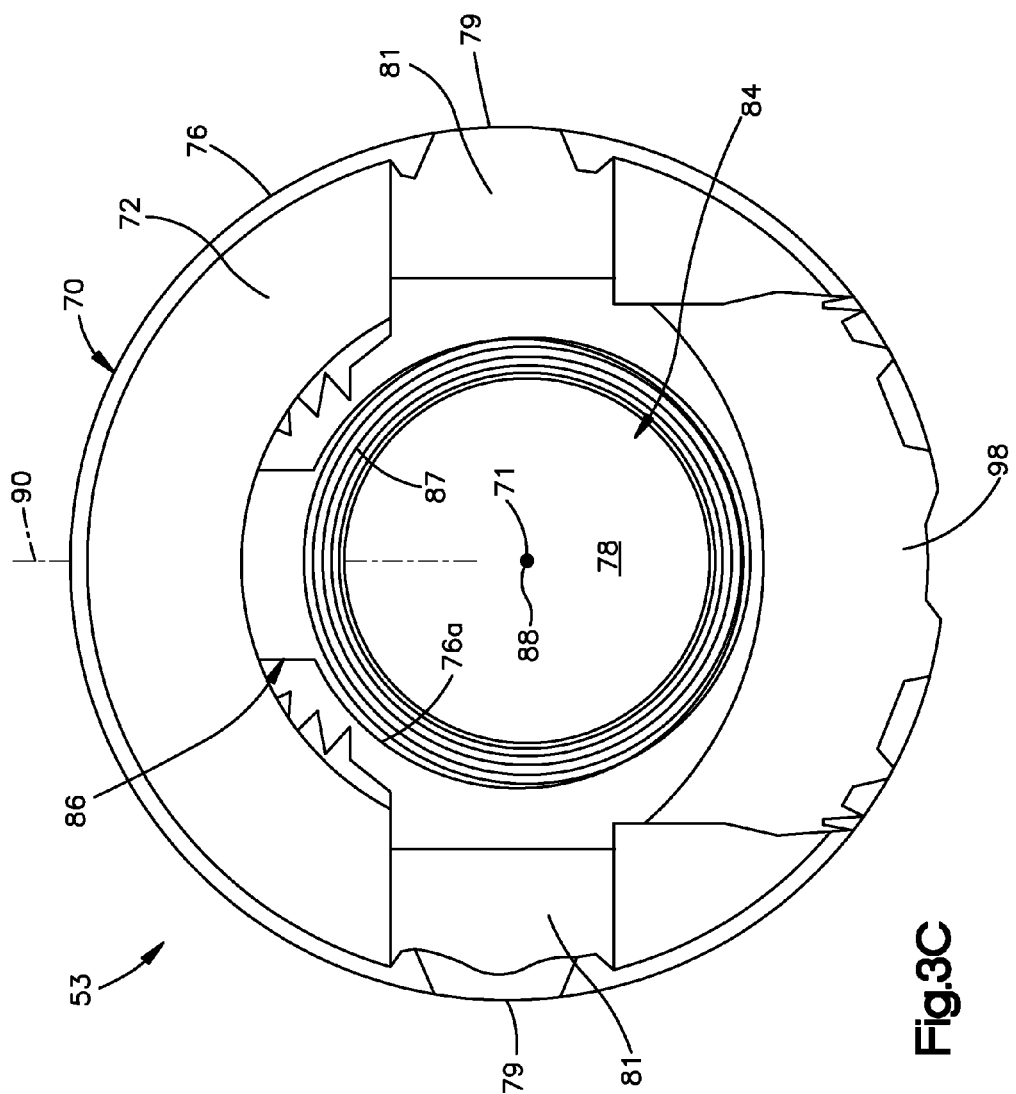
FIG. 3C is a top plan view of the linkage illustrated in FIG. 3A.
Figure 3D:
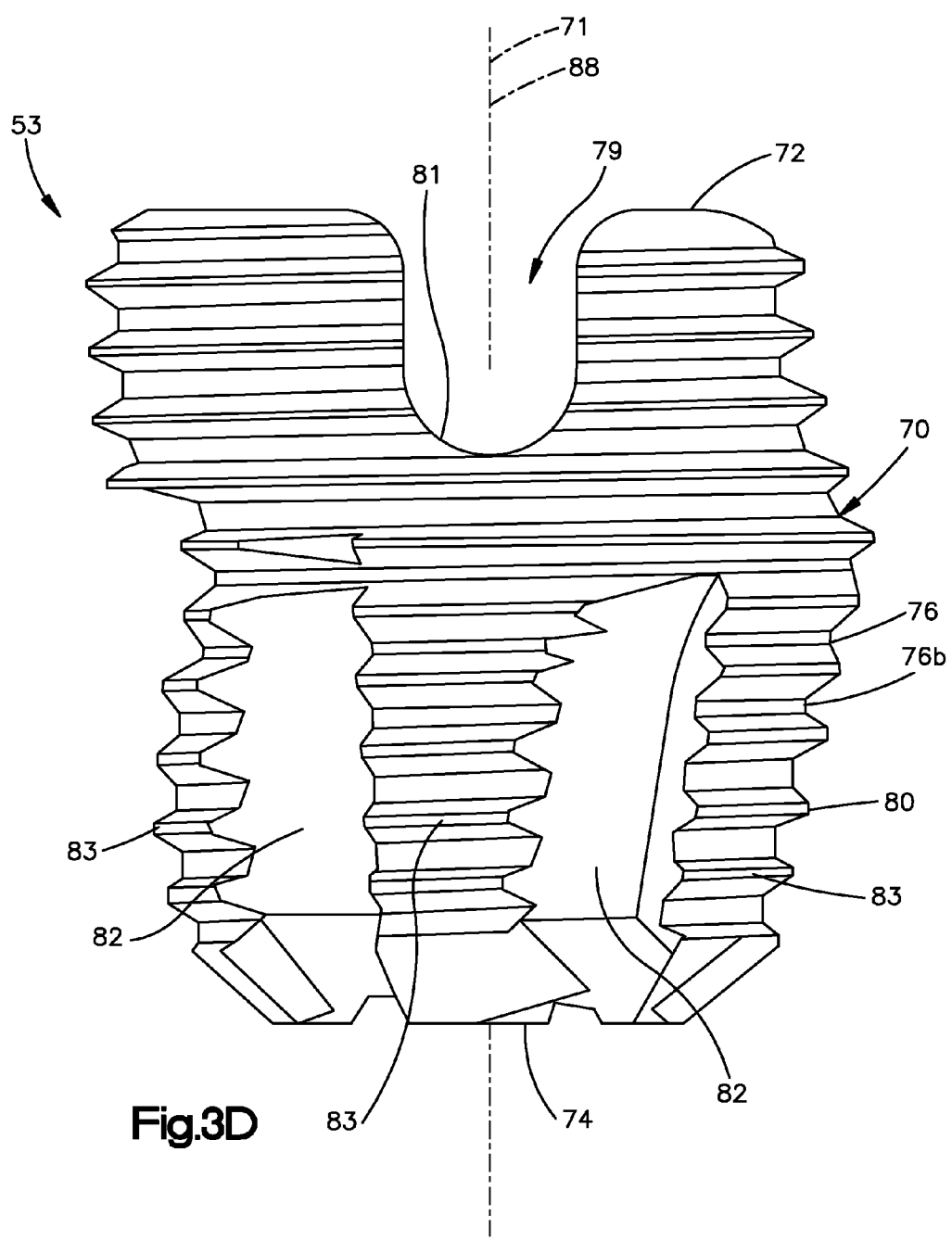
FIG. 3D is a side elevation view of the linkage illustrated in FIG. 3A.

Referring now to FIGS. 2-3D, the linkage 53 is configured to operably couple the first bone anchor 52 and the second bone anchor 54, such that the first and second bone anchors 52 and 54 are fixed with respect to each other. In particular, the linkage 53 is configured to attach to the first and second heads 58 and 64, respectively. In accordance with the illustrated embodiment, the linkage 53 includes a linkage body 70 that extends along a central linkage axis 71, and defines a proximal or upper end 72 and a distal or lower end that 74 that is spaced from the upper end 72 along the central linkage axis 71, and at least one side 76 that extends between the upper and lower ends 72 and 74 and defines an internal void 78 that extends through the linkage body 70 from the upper end 72 to the lower end 74.

The linkage body 70, and in particular the side 76, can be annular about the central linkage axis 71, or alternatively shaped and sized as desired. The at least one side 76 defines an inner surface 76a that defines the internal void 78, and an outer surface 76b that is opposite the inner surface 76a. The outer surface 76b can define any desired shape, and can be substantially circular about the central linkage axis 71 in cross-section in a plane that is normal to the central linkage axis 71. Further, the outer surface 76b can extend substantially parallel to the central linkage axis 71 from the between the upper end 72 and the lower end 74, or can extend toward the central linkage axis 71 as it extends down along a direction from the upper end 72 toward the lower end 74. Alternatively or additionally, the outer surface 76b can be curved as it extends between the upper end 72 and the lower end 74. For instance, the outer surface 76b can be convex.

The linkage 53 can include a pair of drive members 79 that are configured to mate with a driving instrument, such as a screw driver, that applies a torsional force to the linkage 53 and drives the linkage 53 into the threaded aperture of the implant or the bone. For instance, the drive members 79 can be configured as respective first and second opposed recesses 81 that extend into the linkage body 70, for instance into the upper end of the side 76. The recesses 81 can extend from the inner surface 76a through to the outer surface 76b. The recesses 81 can be radially opposite each other such that a straight line 67 that extends between the recesses 81 passes through the central linkage axis 71. The recesses 81 are configured to receive a driving end of the driving instrument. Alternatively, the recesses 81 can be configured as protrusions that are received by the driving instrument.

The linkage 53, and in particular the outer surface 76b, can define threads 80 that are configured to threadedly mate with threads of a complementary threaded aperture, for instance of an implant such as a bone fixation plate, or to purchase with the bone as the linkage 53 is driven into the bone. Alternatively, part or all of the outer surface 76b can be devoid of threads and substantially smooth.

The linkage 53 can further include at least one recess 82, such as a plurality of recesses 82 that extend into the linkage body 70 from the outer surface 76b toward the inner surface 76a. For instance, the recesses 82 can extend toward the central linkage axis 71, but do not extend through the inner surface 76a in accordance with one embodiment. The recesses 82 can divide the threaded outer surface 76b into a plurality of threaded segments 83 that can define cutting flutes that are configured to remove bone material when the linkage 53 contacts bone and is rotated about the central linkage axis 71.

The linkage 53 further defines first and second bores 84 and 86 that extend through the linkage body 70 and are configured to at least partially receive the first and second bone anchors 52 and 54, respectively. For instance, the first bore 84 can be defined by the lower end 74 of the linkage body 70 and can extend into the internal void 78. The lower end 74 of the linkage body 70 that defines the first bore 84 can define internal threads 87 that at least partially surround the first bore 84, such that the first bore 84 can be referred to as a threaded bore. The first bore 84 can extend along a central axis 88 that can be substantially parallel, and coincident, with the central linkage axis 71 of the linkage body 70. Thus, the first bore 84 can extend along the central linkage axis 71. The threads 87 are configured to mate with the external threads 59 of the first head 58 so as to threadedly attach the first head 58 to the linkage 53. The threads 87 can be substantially cylindrical, or can be tapered inwardly, either straight or curved, along a direction from the upper end 72 toward the lower end 74.

In accordance with the illustrated embodiment, the upper end 72 of the linkage body 70 is open, and defines a cross-sectional dimension, such as a diameter, that is greater than the outer cross-sectional dimension, such as diameter, of the first shaft 56. Similarly, the first bore 84 defines a cross-sectional dimension, such as a diameter, that is greater than the outer cross-sectional dimension, such as diameter, of the first shaft 56. Accordingly, the first shaft 56 can be driven substantially down along the central linkage axis 71 through the upper end 72 of the linkage body 70 and the first bore 84. The inner threads 87 of the first bore 84 can be sized substantially equal to the external threads 59 of the first head 58, such that once the first shaft 56 has been driven through the first bore 84, the threads 59 of the first head 58 mate with the threads 87 of the first bore 84 as the first bone anchor 52 is rotated along a first direction about the central axis L1, for instance clockwise, with respect to the linkage body 70. The threads 60 of the first shaft 56 can have substantially the same lead, and the same pitch as desired, as the threads 59 of the first head 58 to facilitate purchase between the first shaft 56 and the bone as the first head 58 threadedly engages the threads 85 of the first bore 84.

It should be appreciated that if desired, the first bone anchor 52 can be removed from the linkage 53. For instance, the first bone anchor 52 can be rotated along a second direction that is substantially opposite the first direction (e.g., counterclockwise) about the central axis L1, so as to disengage the threads 59 of the first head 58 from the threads 85 of the first bore 84, at which point the first bone anchor 52 can be driven up substantially along the central linkage axis 71 and through the upper end 72 of the linkage body 70.

With continuing reference to FIGS. 2-3D, the second bore 86 can extend through the side 76 from the outer surface 76b through the inner surface 76a so as to be open to the internal void 78. Thus, the side 76 can define an interior surface 77 that defines the second bore 86. The second bore 86 can extend along a central axis 90 that can be oriented along a direction that is angularly offset, for instance substantially perpendicular, with respect to the central linkage axis 71 of the linkage body 70 and the central axis 88 of the first bore 84. The central axis 90 intersects the central linkage axis 71 in accordance with one embodiment. The side 76 of the linkage body 70, and in particular the interior surface 77 that defines the second bore 86, can define internal threads 92 such that the second bore 86 can be referred to as a threaded bore. The threads 92 are configured to mate with the external threads 69 of the second head 64 so as to threadedly attach the second head 64 to the linkage 53. The threads 92 can be substantially cylindrical in shape as they extend along a radially outward direction away from the central linkage axis 71, for instance from the central linkage axis 71 toward the second bore 86, or can be tapered inwardly, either straight or curved, along the radially outward direction.

Figure 3E:
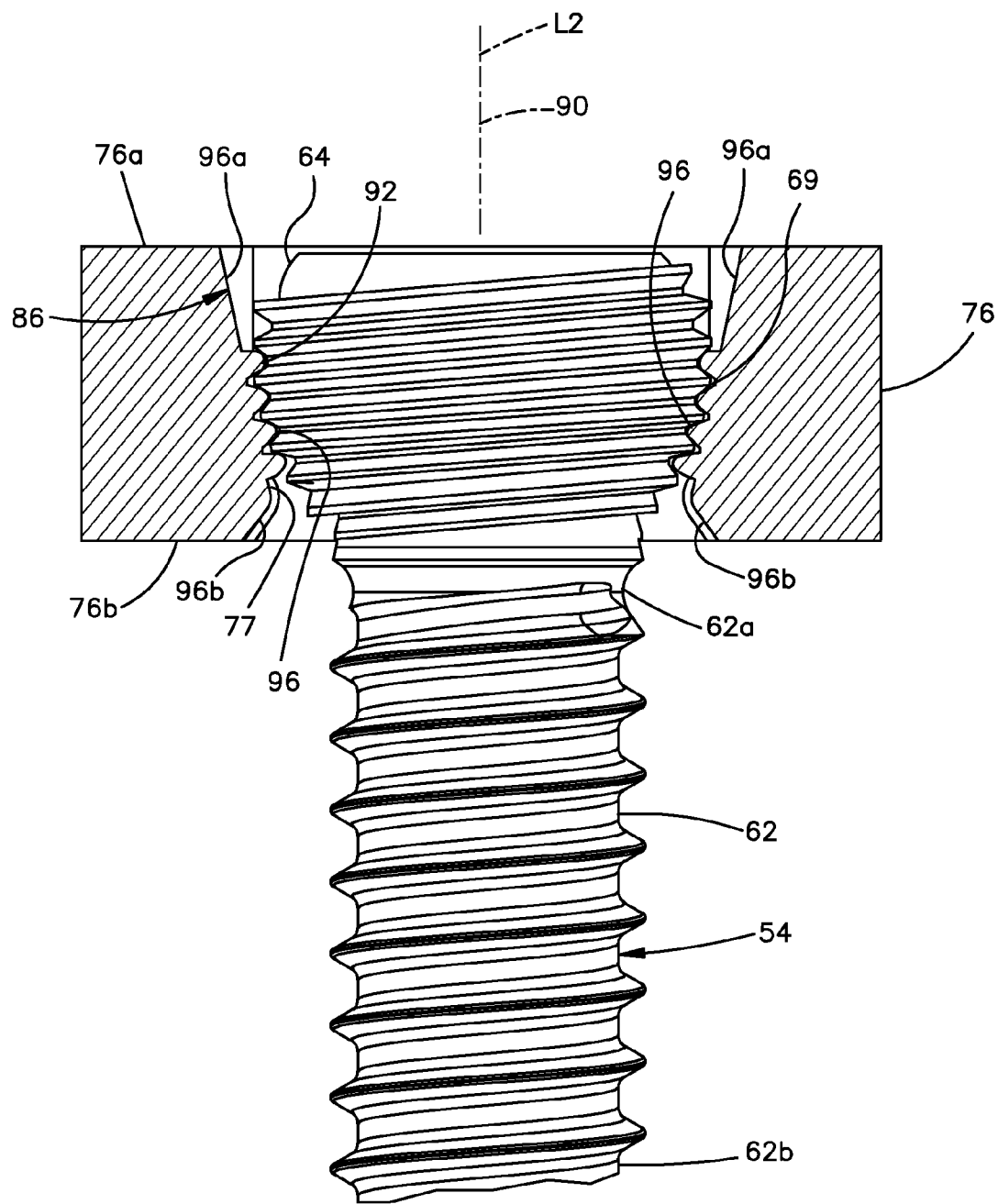
FIG. 3E is a sectional side elevation view of the second anchor inserted into the linkage at a first angle.
Figure 3F:
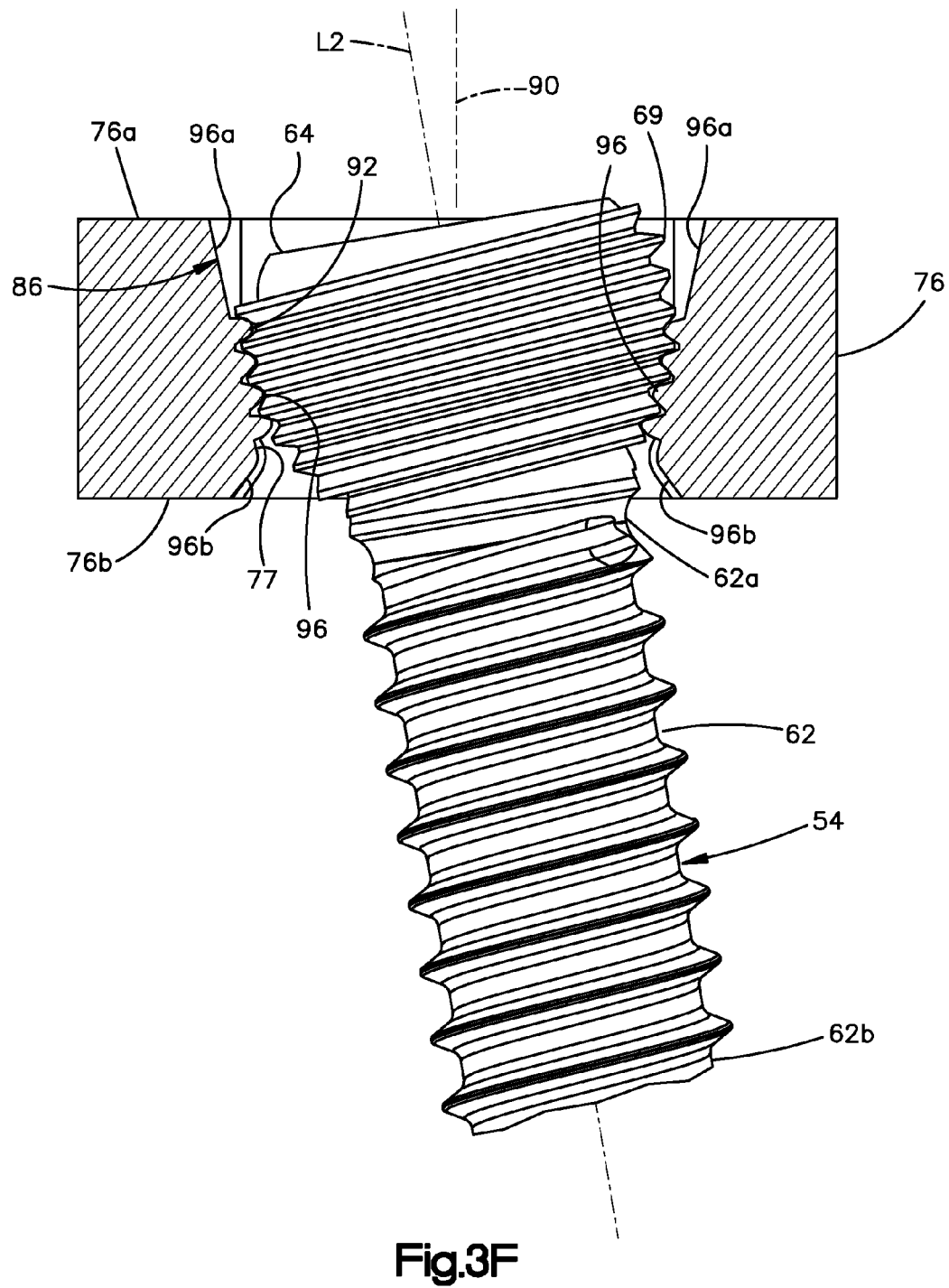
FIG. 3F is a sectional side elevation view similar to FIG. 3E, but showing the second anchor inserted into the linkage at a second angle different than the first angle.

Referring now to FIGS. 2-3F, and as described above, the second bone anchor 54, and in particular the second head 64, is configured to threadedly purchase with the linkage 53, for instance in the second bore 86, such that the angle θ between the first and second central axes L1 and L2, respectively, is adjustable within a range of angulation in the second bone anchor 54 in the second bore 86. Accordingly, an angle α defined by the second axis L2 and the central axis 90 of the second bore 86 is also adjustable within the range of angulation, such that the second axis L2 can be angularly offset with respect to the central axis 90 at any angle as desired within the range of angulation. For instance, the second bone anchor 54 can be inserted into the second bore 86 such that the second axis L2 is coaxial with the central axis 90 or at any angle relative to the central axis 90 within the range of angulation, which can be between and including 0 degrees and 15 degrees. The outer surface of the second head 64 can be round or substantially spherical as illustrated in FIGS. 3E-F, or substantially conically shaped or alternatively shaped as desired.

In accordance with the illustrated embodiment, the interior surface 77 includes a plurality of, for instance four, scalloped portions 94, which can be unthreaded, that extend into the interior surface and interrupt the threads 92. Accordingly, the scalloped portions separate the threads 92 into a corresponding plurality of columns 96 that are spaced from each other, such that ones of the scalloped portions are disposed between adjacent ones of the columns 96 along a circumferential direction about the central axis 90. Each of the scalloped portions 94, the columns 96 and the second head 64 can be shaped substantially as described in U.S. Patent Application Publication No. 2010/0312286, the disclosure of which is hereby incorporated by reference as if set forth herein. In accordance with the embodiment illustrated in FIGS. 3E-F, each of the columns 96 can have any suitable shape as desired. In accordance with the illustrated embodiment, each of the columns 96 has a complex shape including a first portion 96a that tapers radially inward toward the central axis 90 from the outer surface 76b toward the inner surface 76a to a second portion 96b that tapers radially outward from the first portion 96a to the inner surface 76a of the linkage body 70. The first portions 96a of the columns 96 are arranged along a first substantially conical shape centered on the central axis 90 of the second bore 86, and the second portions 96b of the columns 96 are arranged along a second substantially conical shape centered on the central axis 90 of the second bore 86. The scalloped portions 94 between the columns 96 can be, for example, substantially cylindrically shaped and extend radially outward beyond the first and second conical shapes, thereby extending the range of angulation of the second bone anchor 54 when the second bone anchor 54 is inserted into the second bore 86, for instance when the second shaft 62 is angularly aligned with the scalloped portions 94.

In accordance with the illustrated embodiment, the second bore 86 can be defined by four columns 96, spaced about the circumference of the second bore 86 substantially equidistant from one another with widths of the scalloped portions 94, measured circumferentially about the central axis 90, being substantially equal to one another. It should be appreciated, however, that the second bore 86 may include any number of columns 96 arranged in any number of patterns as desired. Furthermore, it should be appreciated that the columns 96 can alternatively be spaced about the circumference of the second bore 86 by varying distances, and the columns 96 and scalloped portions 94 can have different circumferential widths as well.

The first portion 96a of each of the columns 96 can extend radially inward from the outer surface 76b toward the central axis 90 at an angle corresponding to the maximum angulation of the second bone anchor 54 relative to the central axis 90 of the second bore 86. The first portion 96a of each of the columns 96 can further include a corresponding plurality of columns of threads 92 that extend from the interior surface 77 into the second bore 86. Each column 96 may include at least two individual threads 92. However, it will be understood by those of skill in the art that the columns 96 may include any number of threads 92 as desired. The threads 92 are adapted and configured to engage the external threads 69 of the second head 64 and extend, for example, along paths which, if continued across the gaps defined by the scalloped portions 94, would form a helical threading with a substantially constant pitch corresponding to the external threads 69 of the second head 64 of the second bone anchor 54. Alternatively, the threads 92 on each of the columns 96 may be positioned along the first portion 96a of the first column and arranged substantially symmetrically with respect to the threads 92 of the other columns 96.

The second portion 96b of each of the columns 96 extends radially outward with respect to the first portion 96a, for instance from the first portion 96a, toward the outer face surface 76b, for instance to the outer surface 76b, such that the substantially conical portion formed by the second portions 96b of each of the columns 96 is adapted and configured to accommodate the upper end 62a of the second shaft 62 at varying angles within the range of angulation. The spherical shape of the second head 64 permits the external threads 69 to engage the threads 92 of the second bore 86 whether inserted co-axially with the central axis 90 of the second bore 86 as shown in FIG. 3E, or offset from the central axis 90 within the range of angulation, as shown in FIG. 3F.

Referring now to FIGS. 2-3D, the linkage 53 can further include an aperture 98 that provides access to the second bore 86, such that a driver instrument can partially extend through the aperture 98 and engage the drive member 65 of the second bone anchor 54 such that the drive member can apply a torsional force that causes the second bone anchor 56 to drive into bone and further cause the second bone anchor 56 to threadedly attach to the second bore 86. Thus, the linkage 53 can define a straight line that passes through both the aperture 98 and the drive member 65 of the second bone anchor 54, and thus through the second bore 86. In accordance with the illustrated embodiment, the aperture 98 extends radially through the linkage body 70, for instance through the side 76 from the outer surface 76b through the inner surface 76a, and further extends down into the linkage body 70 from the upper end 72 toward, but not to, the lower end 74. The aperture 98 is thus open to the upper end 72 of the linkage body 70, and defines slot that can be elongate along a direction substantially parallel to the central linkage axis 71. The aperture 98 can be radially opposite the second bore 86 such that the straight line that passes through both the aperture 98 and the second bore 86 also passes through the central linkage axis 71. The aperture 98 can further have a circumferential width that can be substantially equal to that of the driver instrument. Accordingly, the driver instrument can angulate within the aperture 98 about a pivot axis that is substantially perpendicular to both the central linkage axis 71 of the linkage body 70 and the central axis 90 of the second bore 86. Thus, the drive instrument and the second bone anchor 54 can angulate along a plane defined by the central linkage axis 71 and the central axis 90, which allows the drive instrument to engage the second drive member 65 when the central axis L2 of the second bone anchor 54 is oriented at any angle within the range of angulation defined by the second bore 86.

The aperture 98 defines a cross-sectional dimension, such as a circumferential cross-sectional dimension, that is greater than the outer cross-sectional dimension, such as diameter, of the second shaft 62. Similarly, the second bore 86 defines a cross-sectional dimension, such as a diameter, that is greater than the outer cross-sectional dimension, such as diameter, of the second shaft 62. Accordingly, the second shaft 62 can be driven substantially down along the central axis 90 through the aperture 98 and further through the second bore 86. The inner threads 92 of the second bore 86 can be sized substantially equal to the external threads 69 of the second head 64, such that once the second shaft 62 has been driven through the second bore 86, the threads 69 of the second head 64 mate with the threads 92 of the second bore 86 as the second bone anchor 54 is rotated along a first direction, for instance clockwise, with respect to the linkage body 70. The threads 61 of the second shaft 62 can have substantially the same pitch as the threads 69 of the second head 64 to facilitate purchase between the second shaft 62 and the bone as the second head 64 threadedly engages the threads 92 of the second bore 86 along any direction within the range of angulation permitted by the second bore 86. It should be appreciated that while the aperture 98 is illustrated as open to the upper end 72 of the linkage body 70, the aperture 98 could alternatively be enclosed by the linkage body 70 as desired.

Figure 4A:
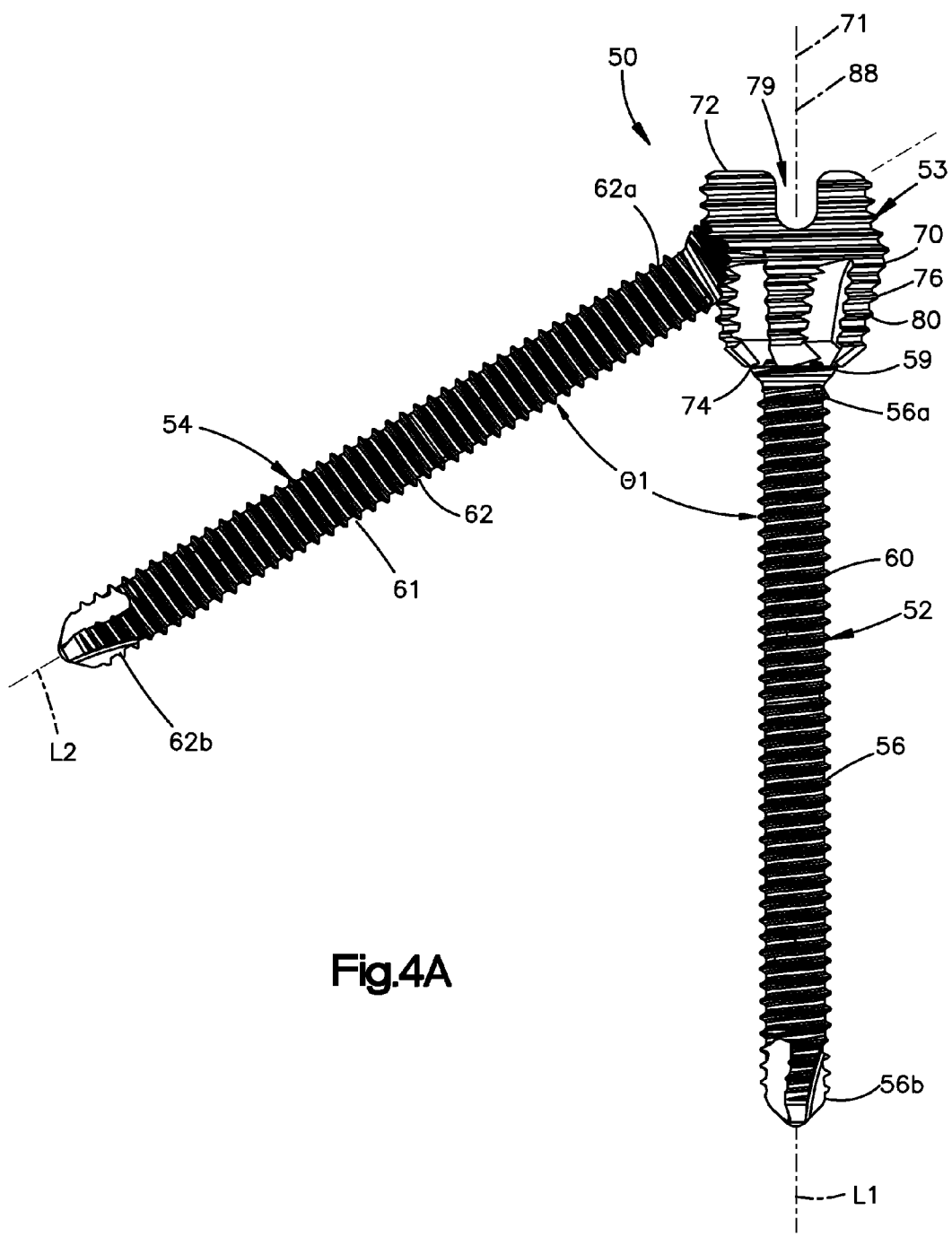
FIG. 4A is a side elevation view of the anchor-in-anchor system illustrated in FIG. 2A, showing the second anchor extending from the linkage along a first direction so as to define a first angle with respect to the first anchor.
Figure 4B:
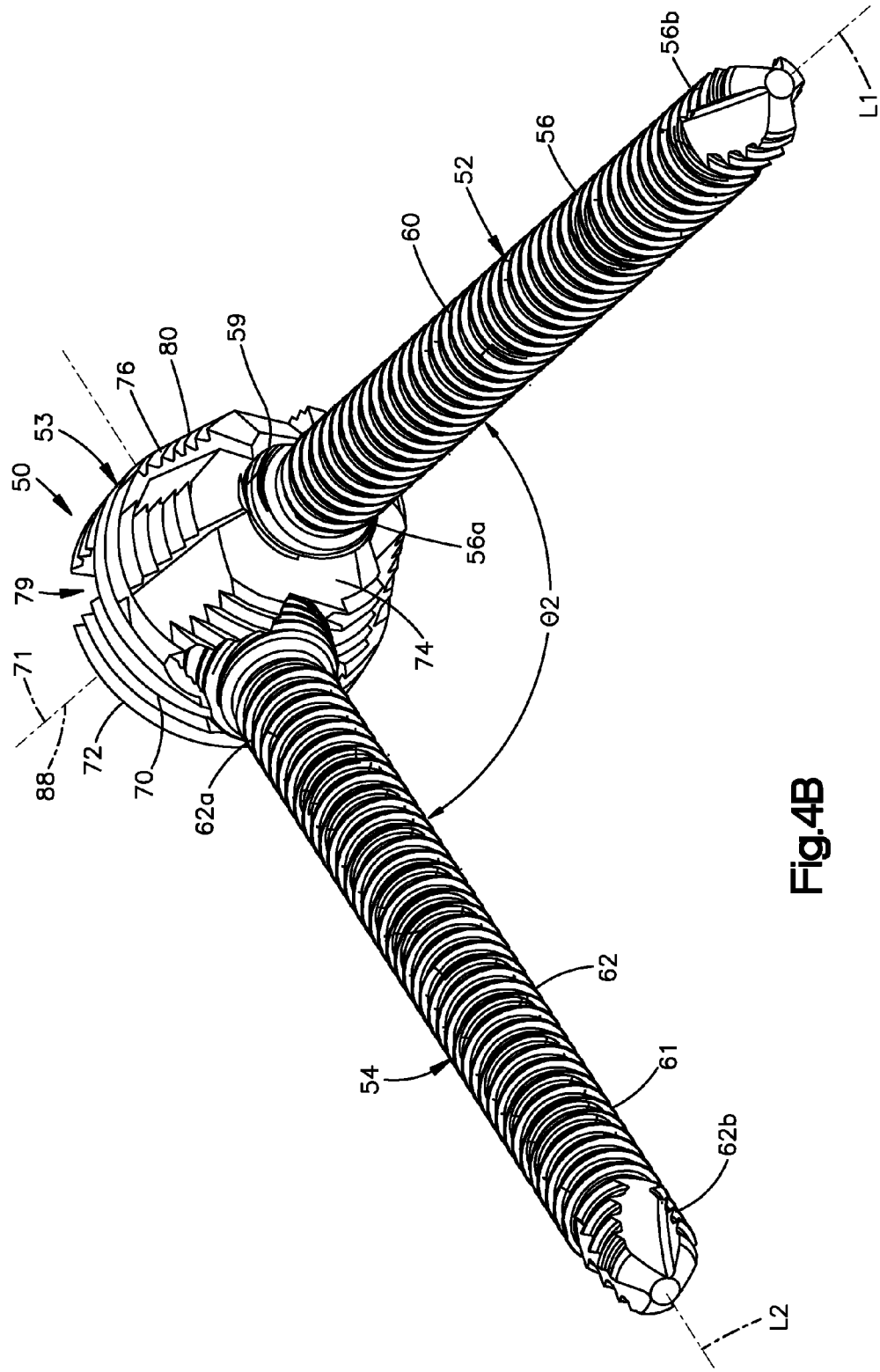
FIG. 4B is a perspective view of the anchor-in-anchor system illustrated in FIG. 4A, showing the second anchor extending from the linkage along a second direction so as to define a second angle with respect to the first anchor that is different than the first angle.
Figure 5A:
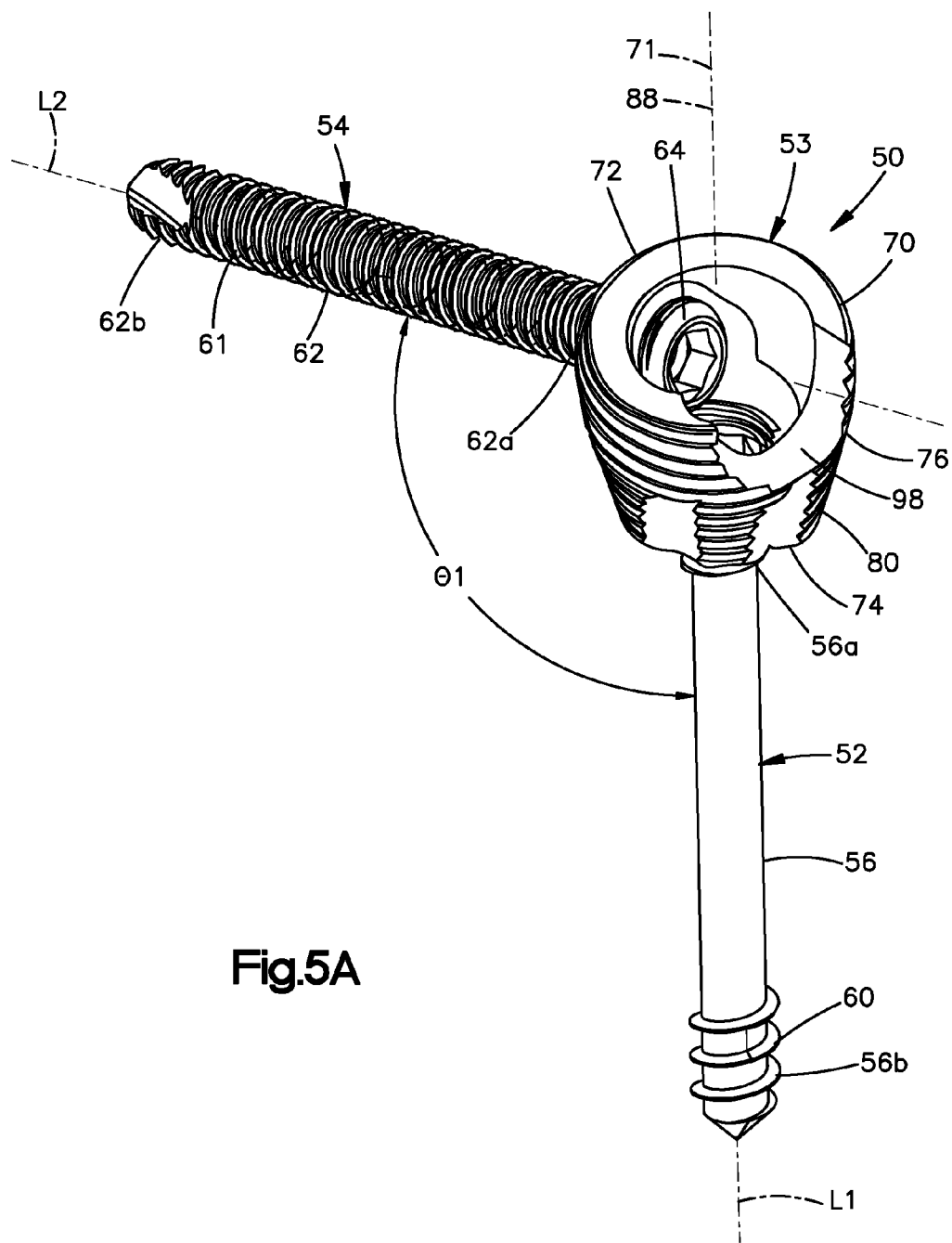
FIG. 5A is a perspective view of an anchor-in-anchor system similar to the anchor-in-anchor system illustrated in FIG. 2A, but showing the first anchor constructed in accordance with an alternative embodiment.
Figure 5B:
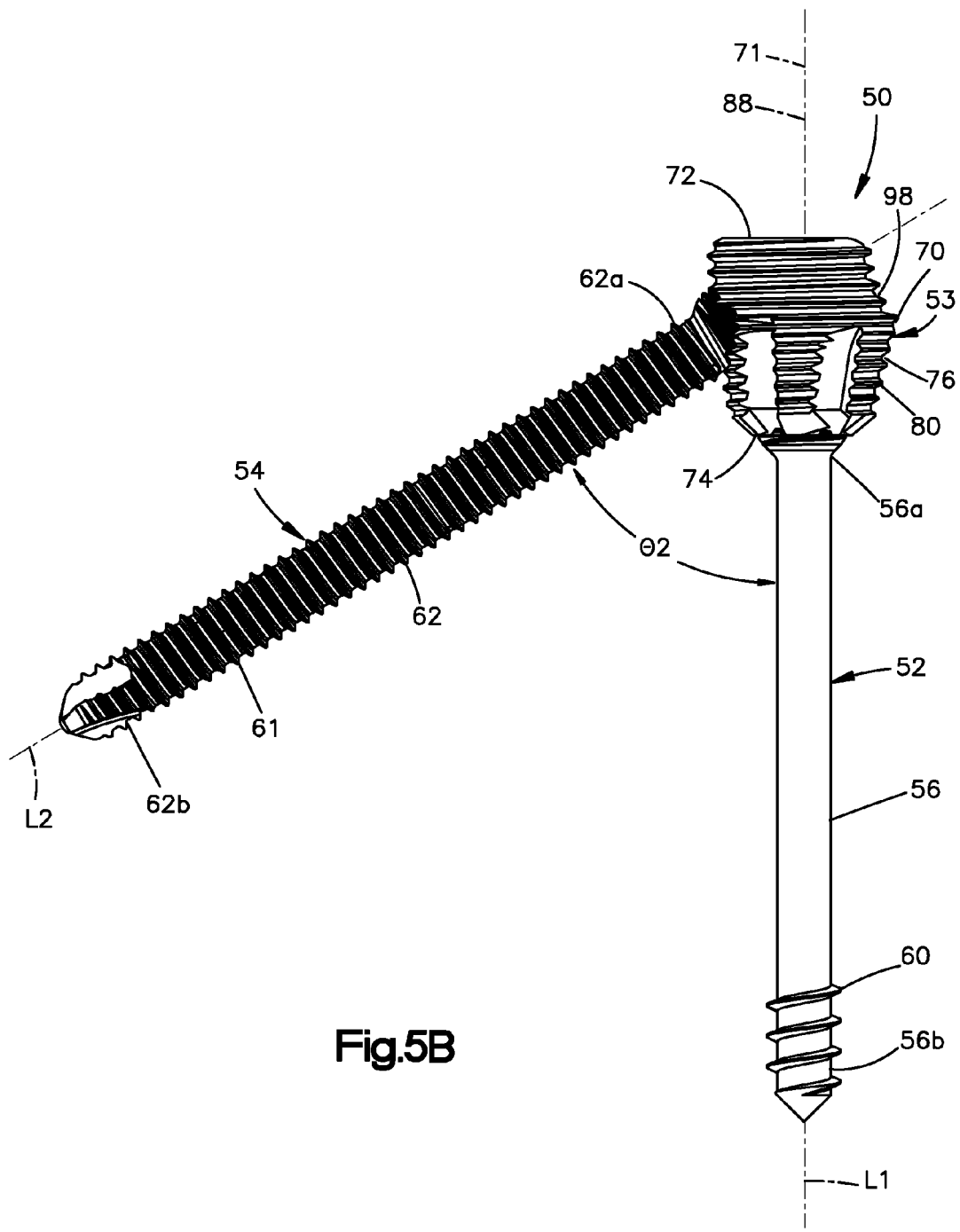
FIG. 5B is a perspective view of the anchor-in-anchor system illustrated in FIG. 5A, but showing the second anchor extending from the linkage along a different direction.

Thus, the second head 64 can mate with the threads 80 of the second bore 86 when the second central axis L2 of the second shaft 62 is oriented oblique to the first central axis L1 of the first shaft 56 so as to define an adjustable angle θ with respect to the first central axis L1, within the range of angles permitted by the second bore 86, as illustrated in FIGS. 4A-5B. For instance, the second bone anchor 54 can mate with the linkage body 70 in the second bore 86 such that the second central axis L2 defines a first angle θ1 with respect to the first central axis L1 as illustrated in FIGS. 4A and 5A, or can mate with the linkage body 70 in the second bore 86 such that the second central axis L2 defines a second angle θ2 with respect to the second central axis L2 that is different than the first angle θ1 as illustrated in FIGS. 4B and 5B. For instance, the second central axis L2 is substantially coincident with the central axis 90 and substantially perpendicular to the first central axis L1 when the second bone anchor 56 is attached to the linkage body 70 within the second bore 86 at an angle of zero degrees, and is oriented oblique (for instance less than 90 degrees) with respect to the first central axis L1 when the second bone anchor 56 is attached to the linkage body 70 within the second bore 86 at an angle of greater than zero degrees. As described above, with respect to FIGS. 1C-D, the first bone anchor 52 can be driven into bone and through an aperture of an implant, such as a bone plate or intramedullary nail, and the second bone anchor 54 can be driven into bone at an adjustable angle with respect to the first bone anchor 52. Furthermore, referring to FIGS. 4A-4B, the first shaft 56 can be threaded substantially along its length, or as illustrated in FIGS. 5A-B can be configured as a lag screw such that the first shaft 56 is threaded only at the distal end 52b, and is smooth between the threads at the distal end 52b and the proximal end 52a.

It should be appreciated that if desired, the second bone anchor 54 can be removed from the linkage 53. For instance, the second bone anchor 54 can be rotated along a second direction that is substantially opposite the first direction (e.g., counterclockwise), so as to disengage the threads 69 of the second head 64 from the threads 92 of the second bore 86, at which point the second bone anchor 54 can be driven up substantially along the central axis 90 of the second bore 86.

While the linkage 53 is illustrated as separate from the first and second bone anchors 52 and 54 and selectively removably attachable to the first and second bone anchors 52 and 54 in the manner described above, it should be appreciated that the linkage 53 can be integral and monolithic with the first bone anchor 52, for instance the first shaft 56, such that the linkage 53 defines the head of the first bone anchor 52 in the manner described above with respect to FIGS. 1A-B, and allows the second bone anchor 54 to be threadedly attached to the linkage 53 at variable angles in the manner described above. Thus, the bore 40 of the first bone anchor 22 illustrated in FIGS. 1A-B can be constructed as described with respect to the second bore 86. Furthermore, while the second bore 86 has been described as being defined by the scalloped portions 94 and the columns 96 that permit the head of the second bone anchor 54 to mate with the second bore 86 within a range of angles, the first bore 84 can alternatively or additionally be defined by the scalloped portions 94 and columns 96 so as to allow the first bone anchor 52 to attach to the lower end 74 of the linkage body 70 at a range of angles with respect to the central linkage axis 71 as described above. Alternatively, the first bore 84 can be configured to only mate with the first head when the first central axis L1 is coincident with the central linkage axis 71 of the linkage body 70.

Although the invention has been described with reference to preferred embodiments or preferred methods, it is understood that the words which have been used herein are words of description and illustration, rather than words of limitation. For instance, it should be appreciated that the structures and features of the various bone fixation assemblies and systems described herein and their components can be incorporated into any of the other bone fixation assemblies and systems described herein and their components, unless otherwise indicated. Furthermore, although the invention has been described herein with reference to particular structure, methods, and embodiments, the invention is not intended to be limited to the particulars disclosed herein, as the invention extends to all structures, methods and uses that are within the scope of the present invention, along with kits having one or more fixation systems, assemblies, or components thereof as described herein. Those skilled in the relevant art, having the benefit of the teachings of this specification, may effect numerous modifications to the invention as described herein, and changes may be made without departing from the scope and spirit of the invention, for instance as recited in the appended claims.

What is claimed:

1. A linkage configured for use in an anchor-in-anchor system, the linkage comprising:

a linkage body defining an open upper end, a lower end, and at least one side having a threaded outer surface and an inner surface opposite the threaded outer surface, wherein the inner surface defines an internal void that extends between the upper and lower ends, the upper and lower ends spaced from each other along a central linkage axis of the linkage body;

wherein 1) the lower end of the linkage body defines a first bore that is open to the internal void, the first bore extending along a central axis, the lower end internally threaded so as to purchase with complementary threads of a first head of a first bone anchor and attach the first bone anchor to the linkage, and 2) the linkage body includes an interior surface that defines a second bore that extends through the linkage body along a central axis that is oblique to the central linkage axis, the interior surface threaded so as to purchase with complementary threads of a second head of a second bone anchor so as to attach the second bone anchor to the linkage.

2. The linkage as recited in claim 1, wherein the central axis of the first bore is substantially coincident with the central linkage axis.

3. The linkage as recited in claim 1, wherein the at least one side is annular.

4. The linkage as recited in claim 1, wherein the outer surface defines a circle about the central linkage axis in a plane that is normal to the central linkage axis.

5. The linkage as recited in claim 1, wherein the outer surface is tapered toward the central linkage axis as the at least one side extends along a direction from the upper end toward the lower end.

6. The linkage as recited in claim 1, wherein the second head is configured to mate with the interior surface at any angle within a range of angles relative to the central axis of the second bore.

7. The linkage as recited in claim 6, further comprising a plurality of scalloped portions that the separate the interior surface into a corresponding plurality of threaded columns.

8. The linkage as recited in claim 7, wherein each of the scalloped portions extends radially outward with respect to the central axis of the second bore.

9. The linkage as recited in claim 8, wherein each of the scalloped portions is unthreaded.

10. The linkage as recited in claim 6, further comprising an aperture that extends through the linkage body from the inner surface to the outer surface, the aperture further extending into the linkage body along a direction from the upper end to the lower end at a location radially opposite the second bore, such that a straight line passes through both the aperture and the second bore.

11. The linkage as recited in claim 1, wherein the linkage body defines a plurality of recesses that extend from the outer surface toward the inner surface.

12. The linkage as recited in claim 11, wherein the recesses do not extend through the inner surface.

13. The linkage as recited in claim 11, wherein the recesses divide the outer surface into a plurality of threaded cutting flutes.

14. The linkage as recited in claim 1, wherein the outer surface defines a plurality of cutting flutes.

15. An anchor-in-anchor system comprising:
a linkage configured for use in an anchor-in-anchor system, the linkage including:
a linkage body defining an open upper end, a lower end, and at least one side having a threaded outer surface and an inner surface opposite the threaded outer surface, wherein the inner surface defines an internal void that extends between the upper and lower ends, the upper and lower ends spaced from each other along a central linkage axis of the linkage body;
wherein 1) the lower end of the linkage body defines a first bore that is open to the internal void, the first bore extending along a central axis, the lower end internally threaded, and 2) the linkage body includes a threaded interior surface that defines a second bore that extends through the linkage body along a central axis that is oblique to the central linkage axis;
a first bone anchor including a first threaded head and a first shaft that extends from the first threaded head along a first central axis, wherein the first threaded head is configured to threadedly attach to the linkage in the first bore; and
a second bone anchor including a second threaded head and a second shaft that extends from the second threaded head along a second central axis, wherein the second threaded head is configured to threadedly attach to the threaded interior surface,
wherein the first central axis is coincident with the central axis of the first bore when the first head is attached to the lower end of the linkage, and the second central axis is oblique with respect to the first central axis when the second head is attached to the interior surface.

16. The anchor-in-anchor system as recited in claim 15, wherein the first head is monolithic with the first shaft, and the second head is monolithic with the second shaft.

17. The anchor-in-anchor system as recited in claim 15, wherein the second head is attachable to the interior surface at a range of angles such that the second central axis defines an adjustable angle with respect to the first central axis.

18. An anchor-in-anchor system comprising:
the linkage recited in claim 1;
the first bone anchor recited in claim 1, further including a first shaft that extends from the first head along a first central axis; and
the second bone anchor recited in claim 1, further including a second shaft that extends from the second head along a second central axis;
wherein the first central axis is coincident with the central axis of the first bore when the first head is threadedly attached to the lower end of the linkage, and the second central axis is oblique with respect to the first central axis when the second head is attached to the interior surface.

19. The anchor-in-anchor system as recited in claim 18, wherein the first head is monolithic with the first shaft, and the second head is monolithic with the second shaft.

20. The anchor-in-anchor system as recited in claim 19, wherein the second head is attachable to the interior surface at a range of angles such that the second central axis defines an adjustable angle with respect to the first central axis.

* * * * *